United States Patent

Krause et al.

Patent Number: 5,670,613
Date of Patent: Sep. 23, 1997

[54] N-VINYL-CONTAINING GLYCOLURIL DERIVATIVES AND THEIR USE AS LIGHT STABILIZERS AND STABILIZERS FOR ORGANIC MATERIAL

[75] Inventors: Alfred Krause, Schwetzingen; Alexander Aumueller, Rieslingweg; Eckhard Korona, Neustadt; Hubert Trauth, Dudenhofen, all of Germany

[73] Assignee: BASF Aktiengesellschaft, Ludwigshafen, Germany

[21] Appl. No.: 495,574

[22] PCT Filed: Jan. 25, 1994

[86] PCT No.: PCT/EP94/00182

§ 371 Date: Aug. 7, 1995

§ 102(e) Date: Aug. 7, 1995

[87] PCT Pub. No.: WO94/18202

PCT Pub. Date: Aug. 18, 1994

[30] Foreign Application Priority Data

Feb. 6, 1993 [DE] Germany .......... 43 03 522.1

[51] Int. Cl.$^6$ .......... C08G 73/06
[52] U.S. Cl. .......... 528/423; 544/180; 544/215; 544/216
[58] Field of Search .......... 528/423; 544/180, 544/215, 216

[56] References Cited

U.S. PATENT DOCUMENTS 4,769,457 9/1988 Helwig et al. .......... 544/180

*Primary Examiner*—James J. Seidleck
*Assistant Examiner*—Duc Truong
*Attorney, Agent, or Firm*—Oblon, Spivak, McClelland, Maier & Neustadt, P.C.

[57] ABSTRACT

N-Vinyl-containing glycoluril derivatives I

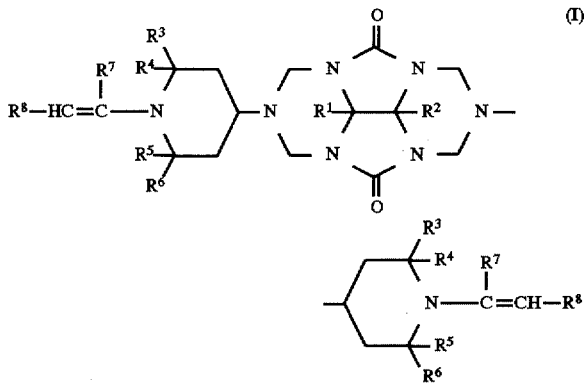

where $R^1$ and $R^2$ independently of one another are each hydrogen, $C_1$–$C_{12}$-alkyl, $C_5$–$C_8$-cycloalkyl, phenyl, tolyl or $C_7$–$C_{12}$-phenylalkyl or $R^1$ and $R^2$ together form a tri-, tetra- or pentamethylene group, $R^3$ to $R^6$ are each $C_1$–$C_4$-alkyl, $R^7$ is hydrogen, $C_1$–$C_8$-alkyl, cyano or a radical of the formula COOR$^9$, $R^8$ is cyano or a radical of the formula COOR$^9$ and $R^9$ is $C_1$–$C_{12}$-alkyl, $C_5$–$C_8$-cycloalkyl, phenyl, tolyl or $C_7$–$C_{12}$-phenylalkyl, are suitable as light stabilizers and stabilizers for organic material, in particular for plastics and coatings.

11 Claims, No Drawings

N-VINYL-CONTAINING GLYCOLURIL DERIVATIVES AND THEIR USE AS LIGHT STABILIZERS AND STABILIZERS FOR ORGANIC MATERIAL

This application is a 371 of PCT/EP 94/00182 filed Jan. 25, 1994.

The present invention relates to novel N-vinyl-containing glycoluril derivatives of the general formula I

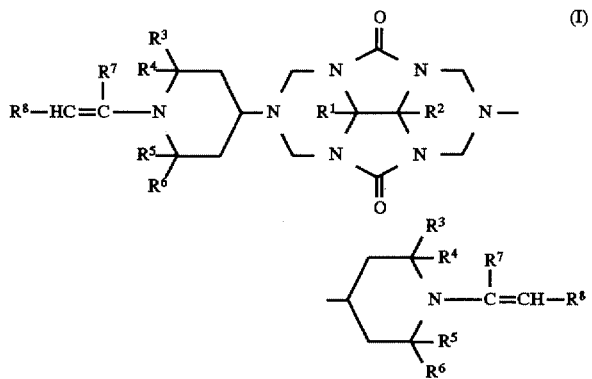

where $R^1$ and $R^2$ independently of one another are each hydrogen, $C_1$–$C_{12}$-alkyl, $C_5$–$C_8$-cycloalkyl, phenyl, tolyl or $C_7$–$C_{12}$-phenylalkyl or $R^1$ and $R^2$ together form a tri-, tetra- or pentamethylene group, $R^3$ to $R^6$ are each $C_1$–$C_4$-alkyl, $R^7$ is hydrogen, $C_1$–$C_8$-alkyl, cyano or a radical of the formula $COOR^9$, $R^8$ is cyano or a radical of the formula $COOR^9$ and $R^9$ is $C_1$–$C_{12}$-alkyl, $C_5$–$C_8$-cycloalkyl, phenyl, tolyl or $C_7$–$C_{12}$-phenylalkyl.

The present invention furthermore relates to a process for the preparation of the compounds I and their use as light stabilizers and stabilizers for organic material, in particular for plastics and coatings, and to organic material stabilized with the compounds I against the action of light, oxygen and heat, in particular stabilized plastics and coatings.

Organic material, in particular plastics and coatings, is known to be destroyed very rapidly, especially by the action of light. This destruction is usually evident in the form of yellowing, discoloration, cracking or embrittlement of the material. With light stabilizers and stabilizers, it is therefore intended to achieve satisfactory protection against the destruction of organic material by light, oxygen and heat.

For example, EP-B 213 570 discloses glycoluril derivatives which are similar to those of the present invention, except that the compounds described there have only hydrogen, chlorine, bromine, hydroxyl, alkoxy, carboxyl, carboxylic ester or unsubstituted or substituted carbamoyl as substituents at the piperidine nitrogen atoms. These compounds are also suitable as stabilizers for organic material.

Such prior art agents are frequently unsatisfactory with regard to their compatibility with plastics, the duration of their protective action, their natural color and their tendency to volatility and thermal decomposition during incorporation at elevated temperatures into the material to be stabilized.

It is an object of the present invention to provide light stabilizers and stabilizers which provide even more effective protection for organic material.

We have found that this object is achieved by the N-vinyl-containing glycoluril derivatives I defined at the outset.

Examples of suitable straight-chain or branched alkyl radicals $R^1$ to $R^7$ and $R^9$, which are mentioned as $C_1$–$C_4$-alkyl radicals, $C_1$–$C_8$-alkyl radicals and $C_1$–$C_{12}$-alkyl radicals, are methyl, ethyl, n-propyl, isopropyl, n-butyl, isobutyl, sec-butyl, tert-butyl, n-amyl, isoamyl, sec-amyl, tert-amyl, neopentyl, n-hexyl, n-heptyl, n-octyl, 2-ethylhexyl, n-nonyl, isononyl, n-decyl, n-undecyl and n-dodecyl. Lower alkyl radicals are generally preferred, especially $C_1$–$C_4$-alkyl, in particular methyl and ethyl.

Particularly suitable $C_5$–$C_8$-cycloalkyl radicals $R^1$, $R^2$ and $R^9$ are cyclopentyl and cyclohexyl, as well as cycloheptyl, cyclooctyl, methylcyclopentyl, dimethylcyclopentyl, methylcyclohexyl, ethylcyclohexyl and dimethylcyclohexyl.

Examples of suitable $C_7$–$C_{12}$-phenylalkyl radicals $R^1$, $R^2$ and $R^9$ are 1-phenylethyl, 2-phenylethyl, 1-phenylpropyl, 2-phenylpropyl, 3-phenylpropyl, 2-phenylprop-2-yl, 4-phenylbutyl, 2,2-dimethyl-2-phenylethyl, 5-phenylamyl, 6-phenylhexyl and especially benzyl.

Suitable tolyl radicals are ortho-, meta- and especially para-tolyl.

In a preferred embodiment, $R^1$ and $R^2$ are each hydrogen, methyl, ethyl, phenyl, tolyl or benzyl, among which hydrogen is very particularly preferred.

In a further preferred embodiment, $R^3$ to $R^6$ are each methyl.

In a further preferred embodiment, $R^7$ is hydrogen, methyl, ethyl, carboxymethyl or carboxyethyl, in particular hydrogen.

In a further preferred embodiment, $R^8$ is carboxymethyl or in particular carboxyethyl.

There are in principle no restrictions regarding the three-dimensional position of the radical $R^8$ at the double bond of I relative to the piperidine ring and to $R^7$. Both E and Z isomers and, where $R^7$ is H, both the cis and the trans isomers may be present. Mixtures of the corresponding cis/trans or E/Z isomers may of course also be present.

The novel N-vinyl-containing glycoluril derivatives I can be advantageously prepared by reacting the corresponding glycoluril derivative unsubstituted at the piperidine N atoms, of the general formula II

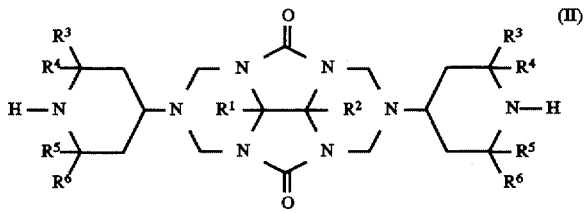

where $R^1$ to $R^6$ have the abovementioned meanings, with an acetylene compound of the general formula III

where $R^7$ and $R^8$ have the abovementioned meanings, in a solvent at from 0° to 200° C.

The compounds II and their preparation are disclosed in EP-B 213 570.

Examples of suitable acetylene compounds III are acetylenedicarboxylic esters, such as dimethyl and diethyl acetylenedicarboxylate, acetylenemonocarboxylic esters, such as methyl and ethyl propiolate, and cyanoacetylene.

The compounds III are Michael acceptors which particularly readily undergo addition reactions with nucleophiles, such as piperidines.

The reaction is advantageously carried out in an organic solvent, in water or in a mixture thereof. Particularly suitable organic solvents are hydrocarbons, such as n-hexane, cyclohexane, methylcyclohexane, n-heptane, benzene, toluene, xylene or mesitylene, nitro- or chlorohydrocarbons, such as methylene chloride, chloroform, carbon tetrachloride, chlorobenzene or nitrobenzene, alcohols, such as methanol, ethanol, n-propanol, isopropanol, n-butanol, isobutanol or butylglycol, carboxylates, such as ethyl acetate, methyl benzoate or butylglycol acetate, and amides, such as dimethylformamide, dimethylacetamide, N-methylpyrrolidone or formamide. An alcohol/water mixture, eg. methanol/water, ethanol/water or isopropanol/water, may also successfully be used as a solvent for the stated reaction. Ethanol alone is particularly preferred.

The reaction is carried out as a rule at elevated temperatures, preferably at from 30° to 180° C., in particular from 50° to 120° C.

The novel compounds I are very useful for stabilizing organic material against the action of light, oxygen and heat. They are also effective as metal deactivators. They are added to the organic material to be stabilized in a concentration of from 0.01 to 5, preferably from 0.02 to 2, % by weight, based on the organic material, before, during or after its preparation.

Organic material is understood as meaning, for example, cosmetic preparations, such as ointments and lotions, drug formulations, such as pills and suppositories, photographic recording materials, in particular photographic emulsions, or intermediates for plastics and coatings, but in particular plastics and coatings themselves.

The present invention furthermore relates to organic material, in particular plastics and coatings, which is stabilized against the action of light, oxygen and heat and which contains the compounds I in the abovementioned concentrations.

All known apparatuses and methods for mixing stabilizers or other additives in polymers may be used for mixing the novel compounds I, especially with plastics.

The organic material stabilized by the novel compounds I may, if required, also contain further additives, for example antioxidants, light stabilizers, metal deactivators, antistatic agents, flame retardants, pigments and fillers.

Antioxidants and light stabilizers which may be added in addition to the novel compounds I are, for example, compounds based on sterically hindered phenols or sulfur- or phosphorus-containing costabilizers.

Examples of such phenolic antioxidants are 2,6-di-tert-butyl-4-methylphenol, n-octadecyl-β-(3,5-di-tert-butyl-4-hydroxyphenyl)-propionate, 1,1,3-tris-(2-methyl-4-hydroxy-5-tert-butylphenyl)-butane, 1,3,5-trimethyl-2,4,6-tris-(3,5-di-tert-butyl-4-hydroxybenzyl)-benzene, 1,3,5-tris-(3,5-di-tert-butyl-4-hydroxybenzyl)-isocyanurate, 1,3,5-tris-[β-(3,5-di-tert-butyl-4-hydroxybenzyl)-propionylethyl] isocyanurate, 1,3,5-tris-(2,6-dimethyl-3-hydroxy-4-tert-butylbenzyl) isocyanurate and pentaerythrityl tetrakis-[β-3,5-di-tert-butyl-4-hydroxyphenyl)-propionate].

Examples of suitable phosphorus-containing antioxidants are tris-(nonylphenyl) phosphite, distearyl pentaerythrityl diphosphite, tris-(2,4-di-tert-butylphenyl) phosphite, tris-(2-tert-butyl-4-methylphenyl)-phosphite, bis-(2,4-di-tert-butylphenyl)-pentaerythrityl diphosphite and tetrakis(2,4-di-tert-butyl-phenyl)-4,4'-biphenylene diphosphite.

Examples of sulfur-containing antioxidants are dilauryl thiodipropionate, dimyristyl thiodipropionate, distearyl thiodipropionate, pentaerythrityl tetrakis(β-laurylthiopropionate) and pentaerythrityl tetrakis(β-hexylthiopropionate).

Further antioxidants and light stabilizers which may be used together with the compounds I are, for example, 2-(2'-hydroxyphenyl)-benzotriazole, 2-hydroxybenzophenones, aryl esters of hydroxybenzoic acids, α-cyanocinnamic acid derivatives, benzimidazolecarboxanilides, nickel compounds or oxalic acid dianilides.

Particularly good stabilization is obtained if at least one further light stabilizer selected from the class of compounds consisting of sterically hindered amines is added in a conventional concentration to the compounds I.

Examples of further suitable sterically hindered amines are bis-(2,2,6,6-tetramethylpiperidyl) sebacate, bis(1,2,2,6,6-pentamethylpiperidyl) sebacate, the condensate of 1-hydroxyethyl-2,2,6,6-tetramethyl-4-hydroxypiperidine with succinic acid, the condensate of N,N'-(2,2,6,6-tetramethylpiperidyl)-hexamethylene diamine with 4-tert-octylamino-2,6-dichloro-1,3,5-triazine, tris-(2,2,6,6-tetramethylpiperidyl) nitrilotriacetate, tetrakis(2,2,6,6-tetramethyl-4-piperidyl)-1,2,3,4-butanetetracarboxylic acid, 1,1'-(1,2-ethanediyl)-bis(3,3,5,5-tetramethylpiperazinone), and the condensates of 4-amino-2,2,6,6-tetramethylpiperidines with tetramethylolacetylenediureas.

Examples of plastics which may be stabilized by the novel compounds I are:

Polymers of mono- and diolefins, for example low density or high density polyethylene, polypropylene, linear polybut-1-ene, polyisoprene, polybutadiene and copolymers of mono- or diolefins or mixtures of the stated polymers;

Copolymers of mono- or diolefins with other vinyl monomers, for example ethylene/alkyl acrylate copolymers, ethylene/alkyl methacrylate copolymers, ethylene/vinyl acetate copolymers or ethylene/acrylic acid copolymers;

Polystyrene and copolymers of styrene or α-methylstyrene with dienes and/or acryloyl derivatives, for example styrene/butadiene, styrene/acrylonitrile (SAN), styrene/ethyl methacrylate, styrene/butadiene/ethyl acrylate, styrene/acrylonitrile/methacrylate, acrylonitrile/butadiene/styrene (ABS) or methyl methacrylate/butadiene/styrene (MBS);

Halogen-containing polymers, such as polyvinyl chloride, polyvinyl fluoride, polyvinylidene fluoride and copolymers thereof;

Polymers which are derived from α,β-unsaturated acids and derivatives thereof, such as polyacrylates, polymethacrylates, polyacrylamides and polyacrylonitriles;

Polymers which are derived from unsaturated alcohols and amines or from their acryloyl derivatives or acetals, for example polyvinyl alcohol and polyvinyl acetate;

Polyurethanes, polyamides, polyureas, polyesters, polycarbonates, polysulfones, polyether sulfones and polyether ketones.

Surface coatings, for example industrial coatings, may also be stabilized using the novel compounds I. Said coatings include baking finishes, among which in turn automotive finishes, preferably two-coat finishes, are particularly noteworthy.

The novel compounds I may be added in solid or dissolved form to the coating material. Their good solubility in coating systems is particularly advantageous.

The novel compounds I are preferably used for stabilizing polyurethanes, polyesters, polystyrene, polyolefins, such as ethylene polymers or propylene polymers, polyamides and ABS and SAN polymers, in particular for stabilizing molding materials consisting of these, and for stabilizing surface coatings.

The novel compounds I are particularly preferably used in powder coatings.

The novel compounds I have good compatibility with the conventional types of plastics, good solubility and excellent compatibility in the conventional coating systems. They have, as a rule, no natural color or only a very slight natural color, are stable and unvolatile at the conventional temperatures for processing plastics and coatings and in particular protect the materials coated with them for a long time.

The examples which follow illustrate the invention. The preparation conditions were not optimized.

PREPARATION EXAMPLE 26 g of ethyl propiolate were added to 50.2 g of the compound of the formula IIa (for preparation, see Example 1 of EP-B 213 570) in 500 ml of ethanol, and the mixture was refluxed for 6 hours. The precipitate obtained after cooling to room temperature was filtered off, washed with 100 ml of n-hexane and dried at 120° C. under reduced pressure from a water pump. 59.2 g of the compound of the formula Ia of melting point 214°–216° C. were obtained.

Calculated C 61.9 H 8.4 N 16.0 Found C 61.6 H 8.4 N 16.0

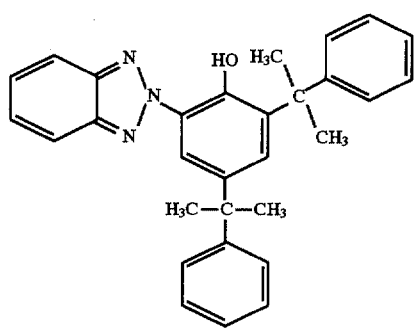

(IV)

(b) Exposure

The samples produced in this manner were weathered for 1900 hours in a Weather-O-Meter having A edge filters. Cracking was evaluated visually under a microscope.

(c) Result

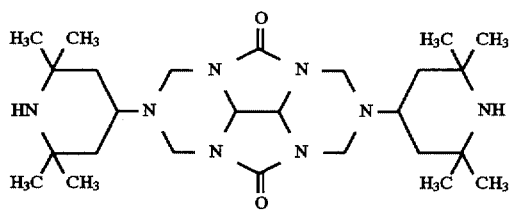

(IIa)

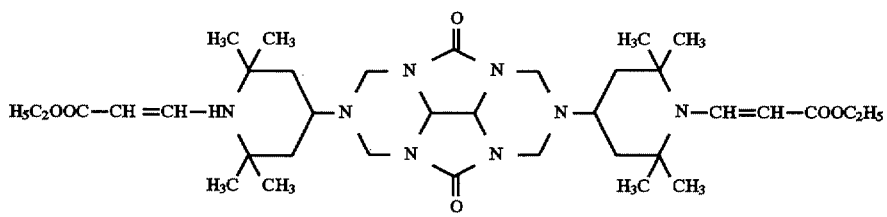

(Ia)

USE EXAMPLE (a) Production of the Test Specimens 980 g of a binder mixture based on hydroxyl-containing acrylate, 12 g of the compound of the formula IV (Tinuvin® 900 from Ciba-Geigy) and 8 g of the novel compound Ia or of the comparative substance IIa were premixed in a high-speed mixer for 4 minutes at 1500 rpm.

The material was extruded and homogenized at a melt temperature of 90°–110° C. in a kneader. The material was cooled and calendered by means of water-cooled nip rolls.

The now brittle material was coarsely comminuted, milled, and sieved to a particle size of ≦100 μm. The material was applied by electrostatic spray coating, in a layer thickness of 60–90 μm, to an aluminum sheet primed with a silver-colored, water-dilutable tinting coat, and the finish was baked at 180° C. for 20 minutes.

The sample obtained using compound Ia according to the preparation example showed no cracking, whereas the comparative sample obtained using compound IIa according to EP-B 213 570 exhibited pronounced cracking.

We claim:

1. An N-vinyl-containing glycoluril derivative of the formula I

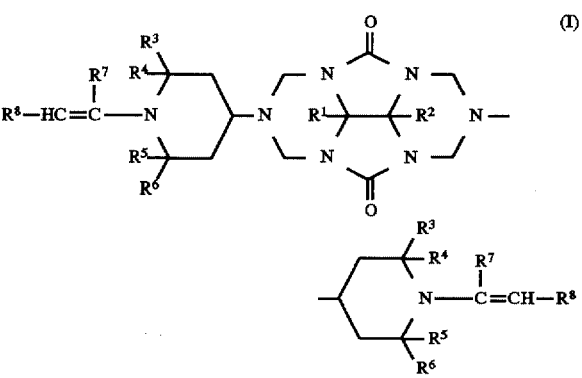

where $R^1$ and $R^2$ independently of one another are each hydrogen, $C_1$–$C_{12}$-alkyl, $C_5$–$C_8$-cycloalkyl, phenyl, tolyl or $C_7$–$C_{12}$-phenylalkyl or $R^1$ and $R^2$ together form a tri-, tetra- or pentamethylene group, $R^3$ to $R^6$ are each $C_1$–$C_4$-alkyl, $R^7$ is hydrogen, $C_1$–$C_8$-alkyl, cyano or a radical of the formula $COOR^9$, $R^8$ is cyano or a radical of the formula $COOR^9$ and $R^9$ is $C_1$–$C_{12}$-alkyl, $C_5$–$C_8$-cycloalkyl, phenol, tolyl or $C_7$–$C_{12}$-phenylalkyl.

2. An N-vinyl-containing glycoluril derivative I as claimed in claim 1, wherein $R^1$ and $R^2$ are each hydrogen, methyl, ethyl, phenyl, tolyl or benzyl.

3. An N-vinyl-containing glycoluril derivative I as claimed in claim 1, wherein $R^3$ to $R^6$ are each methyl.

4. An N-vinyl-containing glycoluril derivative I as claimed in claim 1, wherein $R^7$ is hydrogen, methyl, ethyl, carboxymethyl or carboxyethyl.

5. An N-vinyl-containing glycoluril derivative I as claimed in claim 1, wherein $R^8$ is carboxymethyl or carboxyethyl.

6. A process for the preparation of an N-vinyl-containing glycoluril derivative I as claimed in claim 1, wherein a glycoluril derivative of the formula II

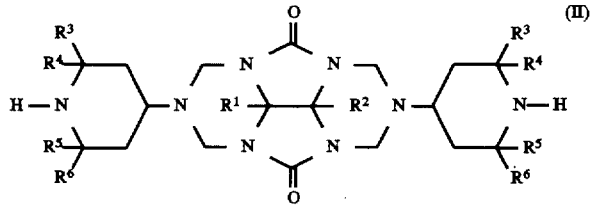

(II)

where $R^1$ to $R^6$ have the abovementioned meanings, is reacted with an acetylene compound of the formula III

(III)

where $R^7$ and $R^8$ have the abovementioned meanings, in a solvent at from 0° to 200° C.

7. A method for stabilizing an organic material against the action of light, oxygen and heat, wherein an N-vinyl-containing glycoluril derivative I as claimed in claim 1 is mixed with said material.

8. A method for stabilizing plastics and coatings against the action of light, oxygen and heat, wherein an N-vinyl-containing glycoluril derivative I as claimed in claim 1 is mixed with said plastics or coatings.

9. An organic material stabilized against the action of light, oxygen and heat, containing from 0.01 to 5% by weight, based on the amount of organic material, of one or more N-vinyl-containing glycoluril derivatives I as claimed in claim 1.

10. A plastic or coating stabilized against the action of light, oxygen and heat, containing from 0.01 to 5% by weight, based on the amount of the plastic or coating, of one or more N-vinyl-containing glycoluril derivatives I as claimed in claim 1.

11. The N-vinyl-containing glycoluril derivative of claim 1, wherein $R^8$ is cyano.

* * * * *